United States Patent
Otvos et al.

(10) Patent No.: US 6,518,069 B1
(45) Date of Patent: Feb. 11, 2003

(54) METHODS AND COMPUTER PROGRAM PRODUCTS FOR DETERMINING RISK OF DEVELOPING TYPE 2 DIABETES AND OTHER INSULIN RESISTANCE RELATED DISORDERS

(75) Inventors: James D. Otvos, Apex, NC (US); Dennis W. Bennett, Shorewood, WI (US)

(73) Assignees: LipoScience, Inc., Raleigh, NC (US); North Carolina State University, Raleigh, NC (US)

( * ) Notice: Subject to any disclaimer, the term of this patent is extended or adjusted under 35 U.S.C. 154(b) by 0 days.

(21) Appl. No.: 09/550,359

(22) Filed: Apr. 19, 2000

Related U.S. Application Data

(60) Provisional application No. 60/130,612, filed on Apr. 22, 1999.

(51) Int. Cl.[7] .......................... G01N 24/08; G01N 33/48
(52) U.S. Cl. ........................... 436/173; 436/71; 436/95
(58) Field of Search ............................ 436/71, 95, 173

(56) References Cited

U.S. PATENT DOCUMENTS

| | | | |
|---|---|---|---|
| 4,933,844 A | 6/1990 | Otvos | 364/413.08 |
| 5,343,389 A | 8/1994 | Otvos | 364/413.09 |
| 5,685,300 A | 11/1997 | Kuenstner | 128/632 |
| 5,770,355 A | * 6/1998 | Brocia | 435/4 |
| 5,869,534 A | * 2/1999 | Bucala et al. | 514/634 |

FOREIGN PATENT DOCUMENTS

| | | |
|---|---|---|
| WO | WO 91/10128 | 7/1991 |
| WO | WO 93/03450 | 2/1993 |
| WO | WO99/32897 | 1/1999 |
| WO | WO99/67623 | 12/1999 |

OTHER PUBLICATIONS

W. T. Garvey et al, Clinical Cornerstone 1998, 1, 13–28.*
W. B. Kannel Am. Heart J. 1985, 110, 1100–1107.*
S. Fan et al, Anal. Chem. 1992, 64, 2570–2574.*
C. J. Sims et al, Am. J. Obstet. Gyn. 1993, 168, 331, abstract 114.*
J. R. Sowers et al, Am. J. Hypertens. 1993, 6, 260S–270S.*
P. D. Zenobi et al, Diabetologia 1993, 36, 465–469.*
S. M. Haffner et al, Diabetologia 1993, 36, 1002–1006.*
M. I. J. Uusitupa et al, Diabetologia 1993, 36, 1175–1184.*
J. Coresh et al, J. Lipid Res. 1993, 34, 1687–1697.*
D. J. Betteridge J. Intern. Med. 1994, 236 (Suppl. 736), 47–52.*
M. P. Stern Diabetes 1995, 44, 3369–374.*

(List continued on next page.)

*Primary Examiner*—Arlen Soderquist
(74) *Attorney, Agent, or Firm*—Myers Bigel Sibley & Sajovec

(57) ABSTRACT

Methods for assessing the risk of developing Type 2 diabetes and other related disorders include obtaining an NMR derived reference spectrum for a known glucose concentration sample and storing this information as a reference standard. A patient blood sample is collected and NMR derived patient spectrums for the blood sample are obtained. The two NMR data sets (the reference and the patient) are compared and a glucose concentration is determined for the patient sample. The glucose concentration can be evaluated with a blood sample undergoing lipoprotein cholesterol evaluation. The NMR based test can be used to concurrently provide a glucose concentration and lipoprotein constituent values based on a single testing event. The disclosure also includes a multi-purpose test, i.e., a test which concurrently provides lipoprotein screening and coronary heart disease risk evaluation along with a diabetes screening and risk assessment for developing Type 2 diabetes. A method for assessing diabetes includes identifying the presence of diabetic dyslipidemia based on the values of predetermined NMR measured lipoprotein constituents.

45 Claims, 7 Drawing Sheets

OTHER PUBLICATIONS

N. Abate et al, Athersclerosis 1995, 118, 111–122.*
S. M. Haffner J. Hypertens. 1995, 13 (suppl. 2) S73–S76.*
T. O'Brien et al, Athersclerosis 1996, 121, 285–291.*
E. Koukkou et al, J. Clin. Pathol. 1996, 49, 634–637.*
R. D. Siegel et al, Metabolism 1996, 45, 1267–1272.*
S. M. Haffner et al, Am. J. Med. 1997, 103, 152–162.*
Arterioscler. Thromb. Vasc. Biol. 1997, 17, 2713–2720.*
H. R. Superko Am. J. Cardiol. 1998, 82, 34Q–46Q.*
R. R. Henry Am. J. Med. 1998 105, 20S–26S.*
S. M. Haffner Diabetes Care 1998, 21, 160–178.*
Z. T. Bloomgarden Clin. Therap. 1998, 20, 216–231.*
M.-R. Taskinen et al, J. Intern. Med. 1998, 244, 361–370.*
A. Garg Am. J. Cardiol. 1998 81, 47B–51B.*
J. Calles–Escandon et al, Coronary Artery Disease 1999, 10, 23–30.*
"Company Profile: LipoMed Technology Anticipated to be a Leading Predictor of Heart Disease," BT Catalyst, Online, pp. 1–3, url:htt;//www.ncbiotech.org/feb98–4.hum (Jun. 8 2000).
"New Test More Accurately Measures Risk of Heart Disease, Study Finds," NC State University Document View, Online, pp. 1–6 (Jul. 13 1998, url:http://search.ncsu.edu (Jun. 8 2000).
Abstracts, Supplement to Circulation, Journal of the American Heart Association Abstracts for the 71st Scientific Sessions (11/98).
Ala–Korpela et al., "Quantification of Biomedical NMR Data Using Artificial Neural Network Analysis: Lipoprotein Lipid Profiles from $^1$H NMR Data of Human Plasma," NMR in Biomedicine, GB, Wiley, London, vol. 8, No. 6, pp. 235–244 (Sep. 01 1995).
Austin et al., "Prospective Study of Small LDLs as a Risk Factor for Non–Insulin Dependent Diabetes Mellitus in Elderly Men and Women," Circulation, vol. 92, No. 7, pp. 1770–17778 (Oct. 1, 1995).
Austin et al., "Small, Dense Low Density Lipoproteins, the Insulin Resistance Syndrome and Noninsulin–Dependent Diabetes," Current Opinion in Lipidology, 7, pp. 167–171 (1996).
Brochure, "New Technology Detects Hidden Risk of Heart Disease; NMR Lipoprofile© Seen as Powerful New Tool in Disease Assessment and Management," LipoMed, Inc., Raleigh, NC (Mar. 26 1998).
Brochure, "NMR LipoProfile©", LipoMed, Inc., Raleigh, NC (on or about Mar. 28, 1998).
Freedman et al., "Relation of Lipoprotein Subclasses as Measured by Proton Nuclear Magnetic Resonance Spectroscopy to Coronary Artery Disease," Arterioscler Thromb Vasc. Biol. 1998; 18:1046–1053 (Jul. 1998).
Kreisberg, "Diabetic Dyslipidemia," Am. Jour. of Cardiology, vol. 82 (12A), pp. 67U–73U (Dec. 17, 1998).
Lamarche et al., "Apolipoprotein A–I and B Levels and the Risk of Ischemic Heart Disease During a Five–Year Follow–up of Men in the Québec Cardiovascular Study," Circulation, vol. 94, No. 3, pp. 273–278 (Aug. 1, 1996).
National Cholesterol Education Program, "Second Report of the Expert Panel on Detection, Evaluation, and Treatment of High Blood Cholesterol in Adults (Adult Treatment Panel II)," Circulation 1994, vol. 89, No. 3 (pp. 1329–1445 (Mar. 1994).
Otvos, "Measurement of Lipoprotein Subclass Profiles by Nuclear Magnetic Resonance Spectroscopy," Handbook of Lipoprotein Testing, pp. 497–508 (AACC Press 1997).
Press Release, "Size Matters—When it Comes to Cholesterol Particles and Heart Disease Risk," LipoMed, Inc., Raleigh, NC (Apr. 14 1999).
Wilson et al., "Predicition of Coronary Heart Disease Using Risk Factor Categories," American Heart Association, Inc. pp. 1837–1847 (May 1998).
Wilson, et al., "Impact of National Guidelines for Cholesterol Risk Factor Screening," JAMA, vol. 262, No. 1, pp. 41–44 (Jul. 7, 1989).
Grant Application to U.S. Public Health Service, entitled "Analysis of Plasma Lipoproteins by IH NMR Spectroscopy," (Jun. 1996).
Phase I Grant Application to U.S. Public Health Service, entitled "Detection of Diabetes Using NMR Spectroscopy," (Dec. 97).
Tilly–Kiesi, Marju, et al., "Hyperinsulinemia And Insulin Resistance Are Associated With Multiple Abnormalities Of Lipoprotein Subclasses In Glucose–Tolerant Relatives Of NIDDM Patients", Journal of Lipid Research, vol. 37, 1996.

* cited by examiner

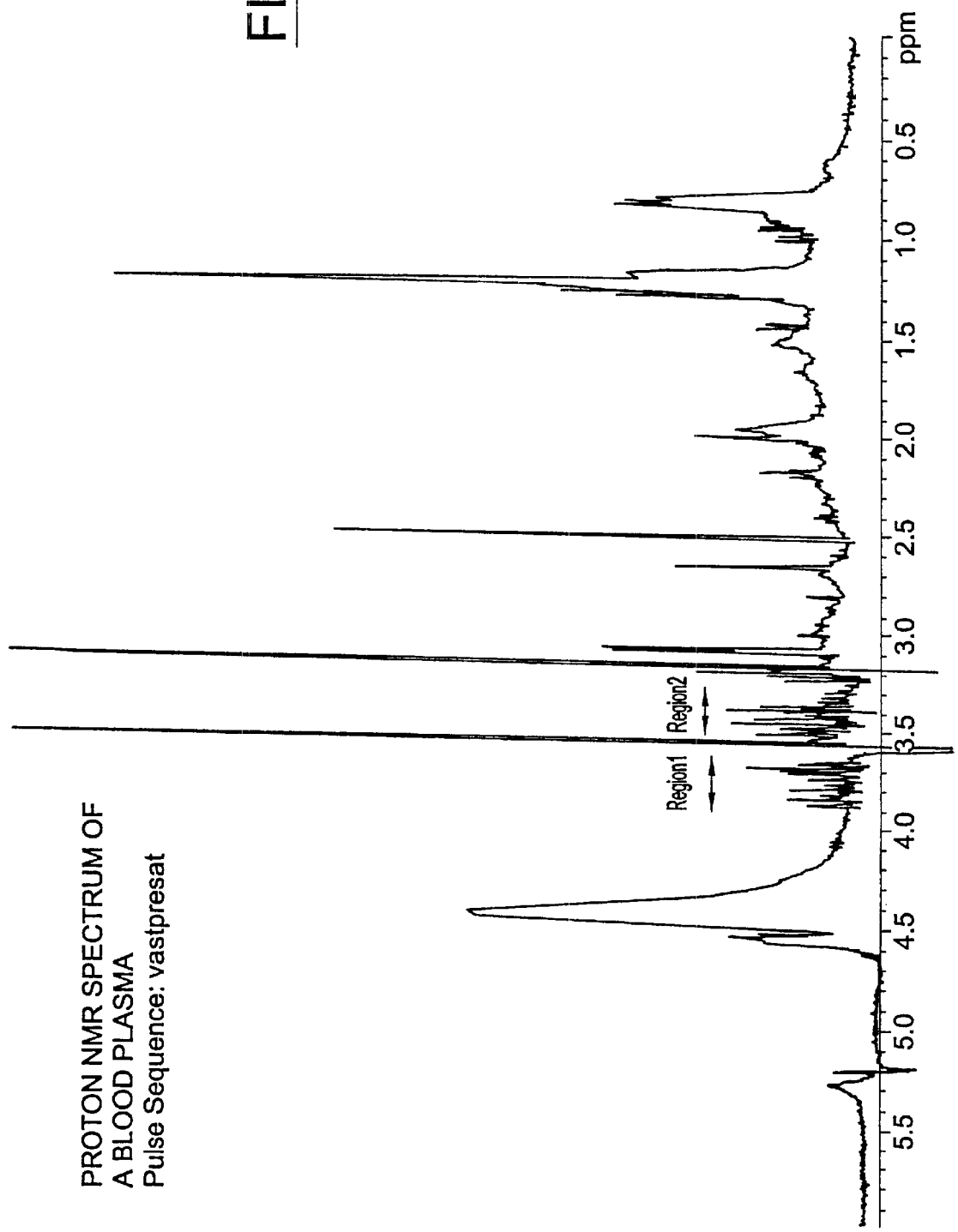

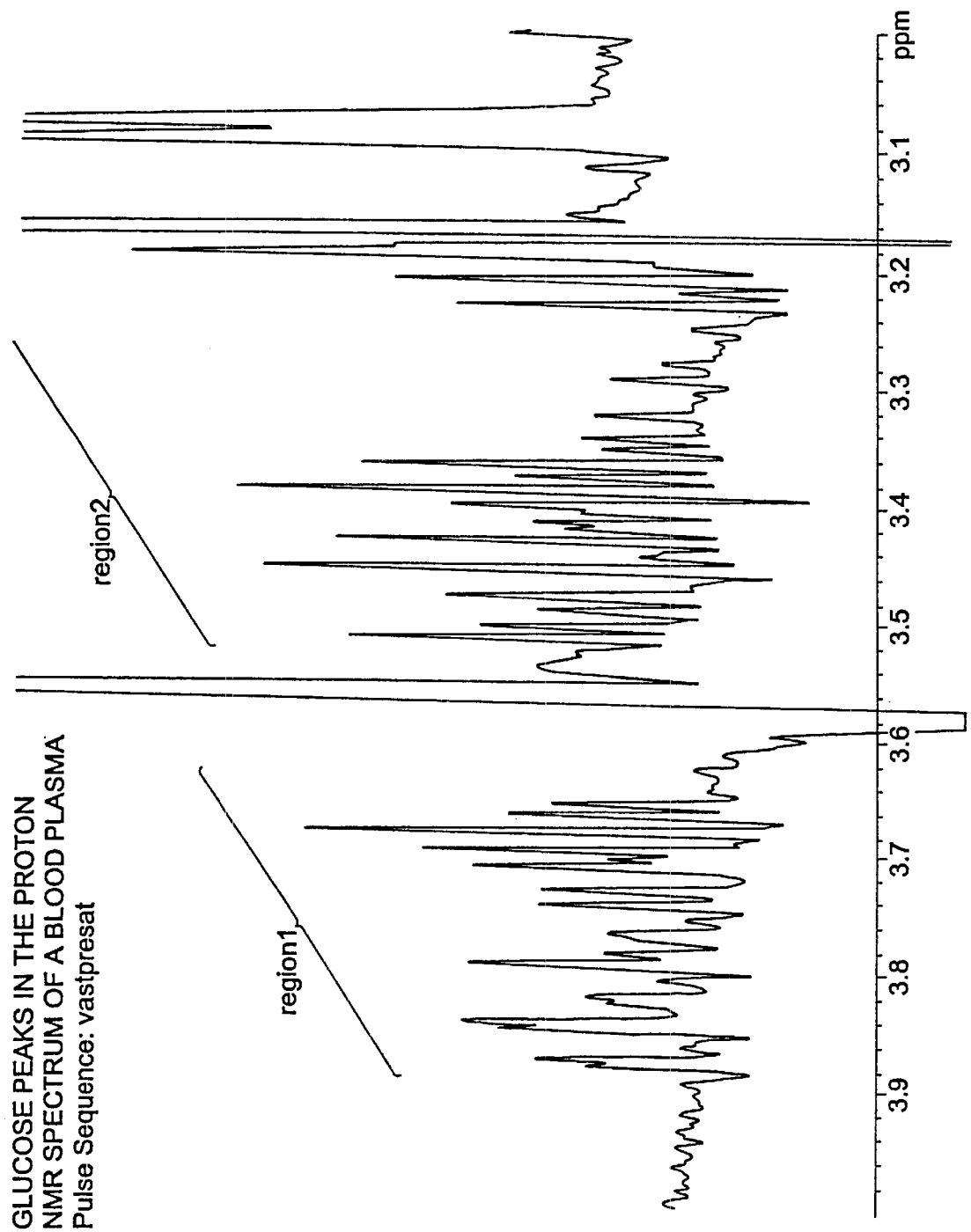

*NMR LipoProfile DM*
Diabetes Report

| Patient Name | Specimen ID | Date Reported |
|---|---|---|
| Patient #5 | LP001141 | 04-05-99 |

TYPE 2 DIABETES RISK ASSESSMENT MODULE

| | mg/dL | Desirable | Moderately Elevated | Diabetes |
|---|---|---|---|---|
| Fasting Glucose | 103 | less than 90 | 90-125 | greater than 125 |

| | | |
|---|---|---|
| Elevated Glucose | >90 mg/dL ✓ | Patients with moderately elevated fasting glucose levels (>90 mg/dL) are at increased risk of becoming diabetic, particularly when they have diabetic dyslipidemia. |
| Diabetic Dyslipidemia | ✓ | Patients with a clustering of the lipoprotein subclass abnormalities listed below are at higher risk of developing diabetes when fasting glucose is moderately elevated. Checks in 2 or more of the boxes below indicate the presence of this metabolic predisposition. |
| • Small LDL | Pattern B ✓ | Small LDL (Pattern B) is a hallmark of "diabetic dyslipidemia" and confers about two-fold higher risk of developing diabetes compared to the large LDL trait (Pattern A). |
| • Low Level of Large HDL | <29 mg/dL ✓ | Only the larger HDL subclasses appear to be protective. Levels of large HDL <29 mg/dL (50th percentile) are associated with increased likelihood of becoming diabetic. |
| • Elevated Level of Large VLDL | >26 mg/dL ✓ | Elevated levels of large, triglyceride-rich VLDL particles in fasting plasma are associated with delayed chylomicron clearance (postprandial lipemia) and increased risk of developing diabetes. Large VLDL levels >26 mg/dL (75th percentile) are considered elevated. |

SUBCLASS LEVELS — Lipoprotein subclass levels (mg/dL) are given in parentheses above each bar. The height of the bar gives the percent of the population* with equal or lower levels.

VLDL Subclasses (mg/dL Triglyceride): Large VLDL (V5+V6) (110) +; Medium VLDL (V3+V4) (163) +; Small VLDL (V1+V2) (13) +

LDL Subclasses (mg/dL Cholesterol): IDL (14) +; Large LDL (L3) (23) +; Medium LDL (L2) (0) +; Small LDL (L1) (105) +

HDL Subclasses (mg/dL Cholesterol): Large HDL (H3+H4+H5) (11) −; Small HDL (H1+H2) (21) +

The plus and minus signs shown above summarize current medical understanding of the relations between lipoprotein subclass levels and heart disease risk. Plus signs signify a positive association with disease (higher levels = higher risk). Larger plus signs signify especially high-risk subclasses. The minus sign signifies a negative association with disease (higher levels = lower risk).

* Population percentile values are from NMR data obtained from analysis of 3,437 subjects in the Framingham Offspring Study.

FIG. 4.

*NMR LipoProfile DM*
Heart Disease Report

| Patient Name | Sex | Age | Physician Name & Address |
|---|---|---|---|
| Patient #5 | | | |

| Patient ID | Birth Date | Specimen ID | Phone:( ) FAX:( ) |
|---|---|---|---|
| | | LP001141 | |

| Date Collected | Date Received | Date Reported | Comments |
|---|---|---|---|
| | 04-02-99 | 04/05/99 | |

SUBCLASS PROFILE

| | | Optimal* | Desirable | Borderline-High | High Risk |
|---|---|---|---|---|---|
| LDL Particle Concentration | nmol/L 1925 | less than 1100 | 1100 - 1399 | 1400 - 1799 | greater than 1800 |

| | | Pattern A (large LDL) | Intermediate Size | Pattern B (small LDL) |
|---|---|---|---|---|
| LDL Size | nm 19.5 | 22.0 - 20.6 | 20.5 - 20.4 | 20.3 - 19.0 |
| | | Lower-Risk | | Higher-Risk |

| | | Negative Risk Factor | Intermediate | Positive Risk Factor |
|---|---|---|---|---|
| Large HDL (cholesterol) | mg/dL 11 | greater than 42 | 42 - 18 | less than 18 |

| | | Lower-Risk | Intermediate | Higher-Risk |
|---|---|---|---|---|
| Large VLDL (triglyceride) | mg/dL 110 | less than 7 | 7 - 33 | greater than 33 |

LDL Particle Concentration categories correspond to NCEP categories for LDL cholesterol (on a percentile equivalence basis) and provide an alternative target for therapy. Large HDL is the protective component of HDL; values <18 mg/dL (20th percentile) indicate higher risk (positive risk factor) and >42 mg/dL (80th percentile) lower risk (negative risk factor). Large VLDL elevations are related to delayed chylomicron clearance and higher CHD risk; values >33 mg/dL (80th percentile) define the "higher-risk" category.

*Goal for secondary prevention (patients with established CHD or diabetes)

CHD RISK ASSESSMENT MODULE

| | | |
|---|---|---|
| Elevated LDL Particle Conc. | >1400 nmol/L ✓ | LDL particle concentration (related to plasma apo B level) may be the single best indicator of LDL-associated CHD risk (Lamarche et al., Circulation 1996;94:273-278) and the best target of risk reduction therapy. Levels>1400 nmol/L (50th percentile) are "elevated". |
| Atherogenic Dyslipidemia | ✓ | Patients with a clustering of the lipoprotein subclass abnormalities listed below are at higher risk of CHD when LDL particle concentration is elevated. Check marks in 2 or more of the boxes below indicate the presence of this higher-risk metabolic condition. |
| • Small LDL | Pattern B ✓ | Small LDL (Pattern B) is a hallmark of "atherogenic dyslipidemia" and confers about three-fold higher risk compared to the large LDL trait (Pattern A). Evidence suggests that small LDL particles may be inherently more atherogenic than large LDL. |
| • Low Level of Large HDL | <29 mg/dL ✓ | Only the larger HDL subclasses appear to be protective, whereas small HDL is positively associated with CHD (Freedman et al., Arterioscler Thromb Vasc Biol. 1998;18:1046-53). Large HDL levels <23 mg/dL (35th percentile) are defined as "low". |
| • Elevated Level of Large VLDL | >17 mg/dL ✓ | Elevated levels of large VLDL subclasses in fasting plasma are associated with CAD severity independently of plasma triglycerides, and are a marker for delayed chylomicron clearance. Large VLDL levels >17 mg/dL (65th percentile) are defined as "elevated". |

FIG. 5.

METHODS AND COMPUTER PROGRAM PRODUCTS FOR DETERMINING RISK OF DEVELOPING TYPE 2 DIABETES AND OTHER INSULIN RESISTANCE RELATED DISORDERS

RELATED APPLICATIONS

This application claims priority from U.S. Provisional Application Ser. No. 60/130,612, filed Apr. 22, 1999.

FIELD OF THE INVENTION

The present invention relates to methods and computer program products for determining whether subjects are at risk for developing Type 2 diabetes and other insulin resistance disorders.

BACKGROUND OF THE INVENTION

Type 2 diabetes, sometimes referred to as adult-onset or non-insulin dependent diabetes mellitus (NIDDM), affects approximately 15 million people in the United States alone. Additionally, approximately 21 million Americans have impaired glucose tolerance or "borderline diabetes" (characterized by high blood sugar levels not high enough to be considered diabetic). Both Type 2 diabetes and borderline diabetes are related to insulin resistance, a condition where the body fails to respond normally to insulin. Insulin resistance is associated with other health problems, including high blood pressure and heart disease. If unchecked, insulin resistance may actually develop into Type 2 diabetes. Type 2 diabetes is associated with a two- to fourfold excess risk of coronary heart disease, and diabetic patients are at an increased risk for morbidity and mortality associated with cardiovascular disease.

Type 2 diabetes has been traditionally diagnosed by the detection of elevated levels of glucose (sugar) in the blood (hyperglycemia). While hyperglycemia is a strong indicator of diabetes, it is a very late stage development in the chain of events that lead from insulin resistance to full-blown diabetes. Accordingly, it would be desirable to have a way of identifying whether or not a subject is at risk for developing Type 2 diabetes (i.e., is predisposed to the condition) prior to the development of the classic symptoms, such as hyperglycemia. Earlier detection of indicators of the disease (e.g., detection of an increase in glucose levels prior to the levels reaching an elevation high enough to be considered hyperglycemia) may lead to more effective treatment of the disease, if not actual prevention of the onset of the disease.

The diagnosis of cardiovascular disorders such as coronary heart disease (CHD) is routinely accomplished by the measurement and analysis of blood cholesterol levels of subjects suspected of having such disorders. In such analyses, total serum cholesterol (TC) is measured, as well as plasma triglyceride levels (TG). Additionally, levels of the major lipoprotein constituents or classes of cholesterol are often measured. These major lipoprotein constituents include low density lipoprotein (LDL), high-density lipoprotein (HDL), and very low-density lipoprotein (VLDL). The major lipoprotein constituents may be further subdivided into subclasses based on further refinement of particle densities. Krauss et al, *J. Lipid Research* 23, 97–104 (1982); Atger et al., *Clinical Chemistry* 37, 1149–1152 (1991). A subclass of lipoprotein particles comprises particles which have common physical properties, such as density. Subclasses distinguished upon density may be considered as a subclass of the class of lipoprotein which contains particles of the subclasses' density.

U.S. Pat. No. 4,933,844 to Otvos describes the use of proton nuclear magnetic resonance ($^1$H NMR) spectroscopy to analyze blood plasma and determine the concentration of the major lipoprotein constituents in a blood plasma sample. U.S. Pat. No. 5,343,389 to Otvos describes the use of $^1$H NMR spectroscopy to analyze blood plasma or blood serum for concentrations of lipoprotein subclasses. The methods described in these patents rely on the fact that $^1$H NMR spectra of human blood plasma contain two prominent peaks centered at approximately 1.2 and 0.8 ppm (relative to a chemical shift standard). These peaks arise from methylene ($CH_2$) and methyl ($CH_3$) protons, respectively, of plasma lipids. Each of these peaks is heterogeneous in nature, consisting of overlapping resonances from protons of the several chemically distinct classes of lipids present in plasma: triglycerides; cholesterol; cholesterol esters; and phospholipids. These lipids are packaged together into the three major classes of lipoprotein particles described above, which differ in density and in the proportions of lipids which they contain. The heterogeneity of these plasma signals is reflected by their complex lineshapes, which vary from person to person owing to variations of the plasma concentrations of the different lipoprotein particles, each of which has its own characteristically different NMR spectral properties. Additionally, lipoprotein subclasses of the major lipoprotein classes or constituents exhibit NMR-measurable properties that are distinct from other subclasses. The NMR properties of one subclass may be distinct in a number of ways, such as chemical shift or lineshape variations, which make the subclass distinguishable from other subclasses.

OBJECTS AND SUMMARY OF THE INVENTION

In view of the foregoing, it is an object of the present invention to provide a more reliable method for determining if a subject is at risk for developing Type 2 diabetes.

It is another object of the present invention to provide a more accurate and/or reliable method for determining if a subject is at risk for developing insulin resistance syndrome.

It is another object of the present invention to provide an improved method for determining if a subject is suffering from insulin resistance syndrome.

It is still another object of the present invention to provide an improved method for evaluating the efficacy of treatment of a subject suffering from Type 2 diabetes.

It is additionally another object of the invention to provide a method of determining the glucose concentration in a blood plasma or blood serum sample ("blood glucose levels"), and further to be able to determine blood glucose levels at sub-hyperglycemic levels.

In order to minimize the necessity of performing numerous, expensive and duplicative tests for determining risk for Type 2 diabetes and disorders of insulin resistance, it is still another object of the invention to provide a method of determining the glucose concentration in a blood plasma or blood serum sample concurrently with determining other lipid-based risk factors for Type 2 diabetes or disorders of insulin resistance.

It is an additional object of the present invention to provide an economical way of screening a subject's blood plasma sample to determine the subject's risk of developing Type 2 diabetes.

It is yet another object of the present invention to provide a computer program product for determining whether a subject is at risk for developing Type 2 diabetes.

These and other objects of the present invention are provided by a method for identifying a patient with an increased risk of developing Type 2 diabetes by analyzing the patient's NMR lipoprotein constituent measurements. Additionally, the risk of the patient developing Type 2 diabetes may further be determined by analyzing the patient's blood glucose levels with NMR spectral analysis. The ability to analyze a patient's blood glucose levels by NMR analysis provides several advantages in that it allows for a blood glucose measurement to be taken concurrently with a patient's lipoprotein constituent measurements, thus avoiding the need for multiple testing events for determining risk for Type 2 diabetes. Additionally, the sensitivity of the NMR-based blood glucose test performed in conjunction with an NMR-based blood lipoprotein test provides an earlier detection of risk for developing Type 2 diabetes. A moderately elevated blood glucose level in the absence of other indicators of risk for developing the disease may not be sufficient to alert a health care provider or a patient that an increased risk of developing the disorder is present. However, a moderately elevated blood glucose level, as detected by the NMR-based methods of the present invention, in conjunction with the presence of other risk factors identified by the NMR-based blood lipoprotein analysis of the present invention, enables a practitioner to determine the risk of developing disorder prior to the onset of the full-blown disease.

In particular, a first aspect of the present invention is a method of determining if a subject is at risk of developing Type 2 diabetes by analyzing a blood sample collected from the subject with NMR spectral analysis. A blood sample, such as blood plasma or blood serum, is collected from a subject. The subject may be a subject that is suspected of being at risk of developing Type 2 diabetes, or may be a subject undergoing a lipoprotein analysis for any other reason (e.g., as a standard screening for cardiovascular disease). The subject may be exhibiting symptoms of Type 2 diabetes, but may alternatively be asymptomatic. The blood sample is then analyzed by NMR spectral analysis.

This NMR-based analysis includes determining a lipoprotein specific constituent identified as being an independently predictive risk factor (in isolation of the other constituent values) and determining a risk associated with a combination of certain of the constituent measurement values. Preferably, the combination method identifies whether the patient's results provide a positive match with key NMR-measured factors. One factor is the determination of the presence of diabetic dyslipidemia (i.e., a clustering of predetermined moderate, borderline, or positive NMR lipoprotein subclass or constituent-based risk values). An additional factor is the detection of at least a moderately elevated NMR-measured glucose level. Advantageously, this type of risk analysis allows for a determination of blood glucose levels prior to an increase in blood glucose levels sufficient to qualify as hyperglycemia (i.e., a moderately elevated blood glucose level that is potentially indicative of Type 2 diabetes can be detected).

Another aspect of the present invention is directed to a method for assessing a patient's risk of developing Type 2 diabetes based on NMR-measured lipoprotein-based information. The method includes generating NMR-based lipoprotein measurement values for a patient's blood plasma or serum sample. The NMR-based lipoprotein measurement values comprise at least one lipoprotein constituent value, but preferably comprise a plurality of lipoprotein constituent values. In a preferred embodiment, the method also includes generating an NMR-based glucose concentration measurement value for a patient's blood serum or blood plasma sample. The plurality of NMR-based lipoprotein constituent values are compared to predetermined test criteria to determine the presence of diabetic dyslipidemia. The NMR-based glucose concentration measurement value is compared to a predetermined test criteria to determine the presence of an increased risk for Type 2 diabetes. A patient's risk of Type 2 diabetes may be assessed based on the presence (or absence) of diabetic dyslipidemia, and on the presence or absence of at least moderately elevated glucose levels.

In a preferred embodiment, the NMR-based lipoprotein constituent measured values include the values associated with LDL size, LDL particles, large HDL cholesterol, and large VLDL triglyceride.

An additional aspect of the present invention is an NMR-based method for measuring the glucose concentration of blood. In this method, an NMR reference data spectrum corresponding to glucose in a reference blood plasma or serum sample or specimen is acquired and stored in computer memory. A reference coefficient is assigned to one glucose signal or group of glucose signals ("reference glucose lineshape") in the reference spectrum, the value of which is based on the glucose concentration of that reference specimen determined by an independent chemical glucose measurement. An NMR spectrum of a patient's blood plasma or serum specimen is acquired at some later time under measurement conditions (substantially) identical to those used to obtain the glucose reference spectrum and stored in computer memory. The reference glucose lineshape is compared with the same glucose signal or group of signals in the patient spectrum ("patient glucose lineshape"). A calculation is then performed which determines the scaling factor needed to adjust the amplitude of the reference glucose lineshape to give the best match with the patient glucose lineshape. This scaling factor is multiplied by the reference coefficient to give the concentration of glucose in the patient blood plasma or serum specimen.

A further aspect of the present invention is a computer program product for personalized NMR-based risk assessment for Type 2 diabetes. The computer program product comprises a computer readable storage medium having computer readable program code means embodied in the medium. The computer-readable program code means comprising computer readable program code means for generating NMR-based lipoprotein measurement values and NMR-based glucose measurement values for a patient's blood sample, the lipoprotein measurement values including at least one subclass variable value. The computer program product also includes computer readable program code means for comparing the at least one patient lipoprotein subclass variable value with predetermined test criteria for determining whether the at least one subclass variable value is associated with a higher or lower risk of developing Type 2 diabetes and computer readable program code means for identifying, for the at least one measured subclass variable value, the corresponding risk level associated with Type 2 diabetes. The computer program product also includes computer readable program code means for providing a risk analysis portion positioned adjacent to the measured lipoprotein values, the risk analysis portion displaying information corresponding to higher and lower risk for Type 2 diabetes. The measured value is visually enhanced in the risk analysis portion to indicate visually the level of risk associated therewith, thereby providing a contemporaneous reference guideline for interpretation of the measured value. The computer program product additionally includes computer readable program code means for comparing a plurality of the NMR-based lipoprotein measurement values to predetermined test criteria to determine the presence of diabetic dyslipidemia. The computer program product also preferably includes computer readable program code means for comparing NMR-based glucose measurement values to predetermined test criteria to determine the presence of elevated blood glucose levels.

In a preferred embodiment, the NMR-based lipoprotein values include the subclass values associated with LDL size, LDL particles, large HDL cholesterol, and large VLDL triglyceride, and the computer program product further comprises computer readable program code means for presenting the lipoprotein measurement values such that each of the lipoprotein measurement values is substantially aligned.

Preferably, for the methods and computer program products described herein, the NMR-measured values include: (a) the LDL size and the concentrations of LDL particles, large HDL cholesterol, and large VLDL triglyceride; and (b) the measured blood glucose level.

The present invention is advantageous because the method described above can accurately and reliably indicate whether a subject is at risk of developing Type 2 diabetes or another insulin resistance disorder, such as insulin resistance syndrome. The method provides advantages over the conventional testing methods for Type 2 diabetes and other insulin resistance disorders in that it can provide an indication of increased risk for the disease prior to the development of symptoms of the disease, such as a blood glucose level high enough to be considered hyperglycemia. By the time these symptoms can be detected with conventional methods, the disorder of Type 2 diabetes (or other insulin resistance disorder) has already progressed to an advanced stage. The NMR-based methods of the present invention can indicate increased risk of developing Type 2 diabetes earlier in the development of disease (i.e., prior to symptom development) because (1) risk factors assessed by the NMR-based lipoprotein analysis provide early indication of disease; and (2) the NMR-based glucose analysis provides for determination of increased glucose levels that are sub-hyperglycemic.

The detection of sub-hyperglycemic glucose levels in the absence of other indicators of risk for developing Type 2 diabetes may not be sufficient to alert the health care provider of a patient that the patient is at risk of developing the disorder. The detection of a sub-hyperglycemic glucose level, made concurrently with the detection of other indicators of risk, however, may allow the health care provider the opportunity for intervention prior to the development of the symptoms of Type 2 diabetes (i.e., hyperglycemic blood glucose levels). The present invention thus facilitates early detection of risk for developing Type 2 diabetes in that an NMR-based test for blood glucose levels may be routinely performed concurrently with an NMR-based test or screen for widely ordered tests typically used to assess coronary heart disease-based (CHD-based) blood lipoprotein values, thus avoiding the additional expense and inconvenience of multiple testing events. The routine screening for those at risk for developing Type 2 diabetes can advantageously facilitate a reduction in the number of individuals advancing into the full-blown disease, thereby providing earlier intervention and potential prevention of the progression into the incurable phase of the disease. The early detection of the disposition for the disorder provided by the present invention thus allows subjects diagnosed as being at risk to begin appropriate treatment or lifestyle changes at an earlier point in time. This early detection is advantageous in that it may lessen the severity of the disease as it progresses, if not actually prevent the onset of the disease. The method of the present invention may also advantageously be incorporated into standard lipoprotein screenings for, e.g., cardiovascular disease.

As described herein, additional aspects of the present invention include methods for determining whether a subject is at risk for developing insulin resistance syndrome (also referred to as Syndrome X). Further aspects of the present invention include methods for determining whether a subject is already suffering from insulin resistance syndrome or another disorder of insulin resistance. In these and other methods of the invention, a blood sample is collected from a subject and analyzed by NMR lineshape spectral analysis as described above. In particular, NMR-based lipoprotein values such as the subclass values associated with LDL size, LDL particles, large HDL cholesterol, and large VLDL triglyceride are measured and compared with predetermined test criteria. The satisfaction of specific test criteria for the relationships between the reference parameters and the measured parameters indicates that the subjects are at risk of developing insulin resistance syndrome, or are in fact suffering from insulin resistance syndrome.

An additional aspect of the invention is a method of evaluating the efficacy of treatment of a subject undergoing treatment for Type 2 diabetes or another insulin resistance disorder. A baseline profile of at least one lipoprotein subclass of the subject undergoing treatment for Type 2 diabetes or another insulin resistance disorder is obtained. This profile is obtained by collecting a blood sample from the subject and analyzing the sample by NMR spectral analysis as described above. This baseline profile may be obtained before the subject has actually commenced treatment for the insulin resistance disorder, or may be obtained after the treatment has begun. A second profile of at least one lipoprotein subclass of the patient undergoing treatment for Type 2 diabetes or another insulin resistance disorder is obtained at a time later than the baseline profile. The second profile is obtained in essentially the same manner as the baseline profile, described above. The baseline profile and the second profile are then compared. The difference between the baseline profile and the second profile provides an indication of the efficacy of treatment for Type 2 diabetes or other disorder of insulin resistance in the subject.

The foregoing and other objects and aspects of the invention are explained in further detail herein.

BRIEF DESCRIPTION OF THE DRAWINGS

FIG. 1 is an NMR spectrum of blood plasma, with the two regions containing signals arising from the protons of blood glucose indicated.

FIG. 2 is a partial NMR spectrum of blood plasma particularly highlighting the two regions containing signals produced by the protons of blood glucose.

FIG. 4 is an illustration of a summary report setting forth a patient's risk for developing Type 2 diabetes according to the present invention.

FIG. 5 is an illustration of a heart disease summary report according to one embodiment of the present invention which may be included in or provided separate from the diabetes risk summary report of FIG. 4.

DETAILED DESCRIPTION OF THE INVENTION

Figure 3A:
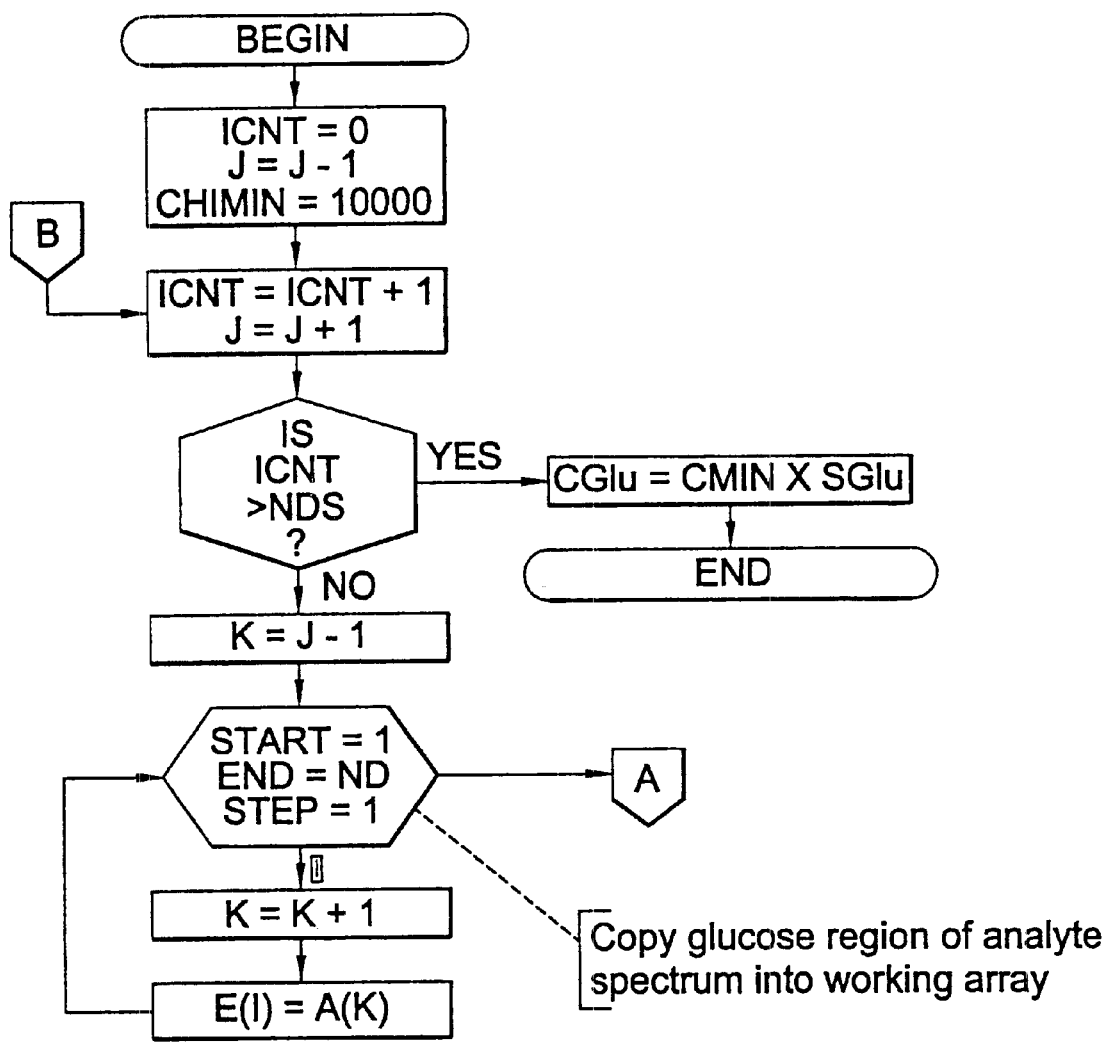
FIGS. 3A–3B together make up a flow chart of a computer program for determining the concentration of glucose in a blood serum or blood plasma sample according to the present invention.

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention is suitable for both medical and veterinary uses. Suitable subjects include, but are not limited to, mammalian and avian subjects; preferably, mammalian subjects; more preferably human, monkeys, pigs, cattle, dogs, horses, cats, sheep, mice, rats, guinea pigs, rabbits, and goats, and are most preferably human subjects.

As used herein, the term "Type 2 diabetes," also and interchangeably referred to as "non-insulin dependent diabetes mellitus (NIDDM)," refers to the disorder characterized by cellular resistance to insulin and/or secretion of less insulin than is necessary to keep blood glucose levels in balance. Type 1 diabetes, in contrast, refers to a disorder characterized by the destruction of insulin producing beta cells in the pancreas by an autoimmune reaction.

The methods of the present invention are useful in the diagnosis of disorders of insulin resistance. Insulin resistance means the failure of the body to respond normally to insulin. Insulin resistance is often a precursor to Type 2 diabetes. "Insulin resistance syndrome" or "Syndrome X" refers to a set of medical conditions related to insulin resistance in which high blood sugar levels stimulate the production of insulin. When a subject is unable to normally process excess insulin, insulin levels rise. Eventually, the subject has high blood sugar levels (hyperglycemia) and high insulin levels (hyperinsulemia). Under these conditions, insulin loses its ability to control fat metabolism, and excessive fats enter the bloodstream (hyperlipidemia). Hyperlipidemia contributes to high blood pressure, heart disease and stroke. Other disorders of insulin resistance, include, but are not limited to, dyslipidemia, (including diabetic dyslipidemia) and full-blown Type 2 diabetes, juvenile diabetes and gestational diabetes.

In addition to diagnosing a subject actually suffering from a disorder of insulin resistance, the methods of the present invention also find use in determining if a subject is at risk for developing Type 2 diabetes (i.e., is predisposed to developing Type 2 diabetes). A subject at risk for developing Type 2 diabetes is any individual who is believed to be at a higher risk than the general population for developing Type 2 diabetes.

In a method of the present invention, a blood sample is collected from a subject. The subject may be suspected of being at risk for developing Type 2 diabetes, or may be suspected of currently suffering from a disorder of insulin resistance. Alternatively, the subject may be undergoing a lipoprotein profile screening for reasons other than suspicion of being at risk for Type 2 diabetes or other insulin resistance disorder (such as screening for coronary heart disease). The blood sample may be collected according to known techniques, and may be a blood plasma sample, or a blood serum sample. The blood sample is then analyzed by NMR spectral analysis, as defined herein, wherein at least one value of at least one lipoprotein constituent is measured.

Preferably, the methods of the instant invention can be routinely included in a standard overall lipoprotein profile analysis protocol for any individual undergoing a lipoprotein profile. Indeed, the methods of the instant invention can be conveniently and quickly automatically run on all lipoprotein profile tests and thereby cost-effectively provide risk information, even while a patient is without symptoms. No additional blood samples are required beyond the standard cholesterol sample and the individual need not be exposed to the relatively time-consuming extended glucose tests. Such a quick and routine test can potentially allow increased numbers of now readily identifiable at-risk patients to undergo drug therapy or lifestyle changes to prevent the onset of insulin resistance disorders.

Examples of lipoprotein constituent values that may be measured in the practice of the present invention include, but are not limited to, the concentration of the lipoprotein constituents and subclasses in the blood sample, and the average particle size of the lipoprotein subclass. The term "lipoprotein constituent," "lipoprotein class" and "major lipoprotein class" are used interchangeably herein. Values of any known lipoprotein constituent (VLDL, HDL, LDL, and chylomicrons) and subclasses of selected constituents may be measured. Lipoprotein subclasses that may be measured are chylomicrons, the six subclasses of very low density lipoprotein (VLDL), which are V1, V2, V3, V4, V5, and V6; IDL; the three subclasses of low density lipoprotein (LDL), which are L1, L2 and L3; and the five subclasses of high density cholesterol (HDL), which are H1, H2, H3, H4, and H5. In the numbering system used to identify the separate lipoprotein subclasses, a lower number indicates a smaller particle size. In the practice of the present invention, at least one value of any one of the lipoprotein subclasses may be measured. Preferably, the value of a plurality of the lipoprotein subclasses will be measured. Still more preferably, the methods of the present invention employ the measurement of at least one value of at least three of the lipoprotein subclasses.

As used herein, the term "NMR spectral analysis" means using proton ($^1$H) nuclear magnetic resonance spectroscopy techniques to measure the lipoprotein classes and subclasses present in blood plasma or blood serum, or to measure the concentration or "level" of glucose present in blood plasma or blood serum as described herein. "Measuring" a lipoprotein class or subclass refers to determining a parameter of the lipoprotein class or subclass, such as the concentration of the lipoprotein class or subclass or the average particle size thereof. More specifically, the method includes acquiring proton NMR data from a sample of blood plasma or serum, processing the acquired NMR data to produce a chemical shift spectrum, and deconvoluting the spectrum in terms of the reference spectra of subclasses of the major classes of lipoprotein to give the concentration of each of the lipoprotein constituents and the distribution of subclasses of the constituents. The method also includes acquiring proton NMR data from a sample of blood plasma or serum, processing the acquired NMR data to produce a chemical shift spectrum, and deconvoluting the spectrum in terms of the reference spectrum of glucose to give the concentration of glucose in the blood serum or blood plasma sample.

In a preferred embodiment, the concentrations of the lipoprotein classes and/or subclasses are determined by acquiring reference spectra of individual lipoprotein classes and/or subclasses. The reference spectra are then stored, such as in a computer program, to provide a reference basis for evaluating additional blood samples or serum samples. The NMR spectroscopy-derived spectra associated with the individual lipoprotein classes and subclasses are substantially invariant across the population. As such, the NMR reference spectra (lineshapes and amplitudes) of individual lipoprotein constituents can be used as a "key" to "deconvolute" the composite signal associated with an individual's whole blood plasma (or blood serum). In this way, a single reference set can be used as a basis to determine the lipoprotein profile of other blood samples (when taken at a substantially constant temperature and magnetic field).

More particularly stated, one embodiment of the present invention assigns a scalable coefficient to the individual reference constituent standards and takes the sums of the scalable (weighted) individual constituent parameters. An NMR spectroscopy analysis is generated for a desired blood plasma or serum specimen (taken at the same magnetic filed strength and temperatures used for the reference spectra) to provide an actual (measured) composite blood plasma spectra signal. The preferred method of the present invention then manipulates the scalable reference spectra until the sum of the scalable coefficients substantially "fits" the composite signal value. The value of the scalable coefficient is then used to determine the actual concentration values for the lipoprotein constituents in the blood plasma sample of that individual.

Advantageously, the preferred NMR spectroscopy analysis can (relatively quickly) extract from the $^1$H NMR spectrum the concentrations of the three major lipoprotein classes (VLDL, LDL, and HDL) of a plasma sample as well as a multiplicity of subclass information. As described above, the NMR spectroscopy method preferably identifies and uses four individual constituents (VLDL, LDL, HDL, and proteins) of a reference blood sample to deconvolute the lineshapes associated with the whole blood plasma lipids. Indeed, as noted in U.S. Pat. No. 4,933,844 to Otvos, the substantially invariant lineshape of the NMR spectra of the individual lipoprotein constituents across the population can be used as a "key" to manipulate the composite signal with a derived mathematical analysis. Further details of the preferred NMR spectral analysis are described in U.S. Pat. Nos. 4,933,844 and 5,343,389, both to Otvos, the specifications of which are hereby incorporated by reference herein in their entireties as if set out fully.

In addition to determining parameters of the lipoprotein classes LDL, HDL, and VLDL, and the subclasses thereof in blood, the NMR spectral analysis of the present invention may also be used to measure the parameters of other constituents of blood such as the concentration of triglycerides, protein, and chylomicrons in the blood sample.

In an additional embodiment of the invention, the concentration of glucose in a blood sample of the present invention is determined using the $^1$H NMR techniques described herein. In a preferred embodiment of the invention, the concentration of glucose in a blood sample of the invention is measured using NMR spectral analysis concurrently with the NMR-based measurement of lipoprotein values in the same blood sample. As used herein, the word "concurrently" means sufficiently close in time to be able to be performed during one NMR "run" or measurement event (that is, "concurrently" may be simultaneously, or it may be two or more events occurring within a short time period before or after each other, or it may be an NMR evaluation performed on the same sample, or samples taken from the patient in a single blood withdraw session, or samples taken from a single venipuncture once patency is established).

Patients with moderately elevated fasting glucose levels are at an increased risk of developing Type 2 diabetes, particularly if other indications of diabetic dyslipidemia are present. Accordingly, the present method allows for the determination of the concentration of glucose in a sample of blood plasma by $^1$H NMR spectral analysis. This is done by comparing the $^1$H-NMR spectrum of the sample to the spectrum of a sample with a known glucose concentration. By comparing the difference in intensities of the sample spectra, the concentration of glucose in the spectrum can be calculated.

FIG. 1 shows the proton NMR spectrum of blood plasma, with the two regions (region 1 and region 2) containing the signals produced by glucose indicated. FIG. 2 shows an expansion of the region of the blood plasma spectrum where glucose signals are observed, the two regions being specifically indicated as region 1 and region 2. The peaks in region 1 in the range of 3.64–3.90 ppm can be used for glucose analysis according to the present invention. Alternatively, the peaks in region 2 in the range of 3.29–3.54 ppm can be used for the glucose analysis of the present invention. Additionally, the combination of the peaks in region 1 and region 2, may be used for the quantitative determination of glucose according to the present invention. The data points in the reference or standard spectrum and patient glucose sample spectra are aligned using a line-shape fitting process as described herein to find the "best fit," and the intensity of the standard spectrum is scaled to match the sample spectrum. The glucose concentration of the standard is multiplied by the scaling factor used to match the sample lineshape to give the glucose concentration of the blood sample.

Stated differently, in this glucose measurement method, an NMR reference data spectrum corresponding to glucose in a reference blood plasma or serum sample or specimen is acquired and stored in computer memory. A reference coefficient is assigned to one glucose signal or group of glucose signals ("reference glucose lineshape") in the reference spectrum, the value of which is based on the glucose concentration of that reference specimen determined by an independent chemical glucose measurement. An NMR spectrum of a patient's blood plasma or serum specimen is acquired at some later time under measurement conditions (substantially) identical to those used to obtain the glucose reference spectrum and stored in computer memory. That is, for example, the NMR data spectrums are obtained under the same magnetic field strength and specimen temperature. The reference glucose lineshape is compared with the same glucose signal or group of signals in the patient spectrum ("patient glucose lineshape"). A calculation is then performed which determines the scaling factor needed to adjust the amplitude of the reference glucose lineshape to give the best match with the patient glucose lineshape. This scaling factor is multiplied by the reference coefficient to give the concentration of glucose in the patient blood plasma or serum specimen.

The mathematics used in the lineshape fitting process (i.e., least squares fit of an unknown function in terms of a weighted sum of known functions) is well known and is described in many textbooks of numerical analysis such as F. B. Hildebrand, *Introduction to Numerical Analysis*, 2nd edition, pp. 314–326, 539–567, McGraw-Hill, 1975. A flow chart illustrating a computer program used to calculate the concentration of glucose in a patient's blood serum or blood plasma sample is set forth in FIGS. 3A and 3B. In the flow chart of FIGS. 3A and 3B, the terms are defined as follows.

Sglu means the concentration of glucose in the reference standard. Cglu is the concentration of glucose in the patient sample. J means data point in the patient spectrum to begin search for best least squares fit (increments as ICNT increments). NDS means the number of data points to traverse sequentially in search for best least squares fit. ICNT corresponds to the counter for sequential search, which begins at 1 and ends at NDS.

A(1), A(2), A(3) . . . A(NDAT) indicates the array containing NDAT data points from the patient blood sample NMR spectrum.

ND indicates the number of data points in the reference standard glucose NMR spectrum.

G(1), G(2), G(3) ... A(ND) indicates the array containing data points from the standard glucose NMR spectrum.

E(1), E(2), E(3) ... A(ND) indicates the array containing data points from the patient blood sample NMR spectrum in selected NMR spectral region containing glucose resonances (i.e., from the same region as standard).

The term CHIJ represents the least squares variance for best fit to the sample region beginning with the Jth data point.

The term CJ represents the calculated coefficient multiplying the data points in the standard glucose array G( ) to give the best fit to the patient sample region beginning with the Jth data point.

The term CHIMIN represents the smallest least squares variance found in the spectral search (initialized as a large positive number to be replaced by first fit in search sequence).

The term CMIN represents the calculated coefficient multiplying the data points in the standard glucose array G( ) to give the best fit in the patient spectral region beginning at the data point for which CHIMIN is determined.

Figure 3B:
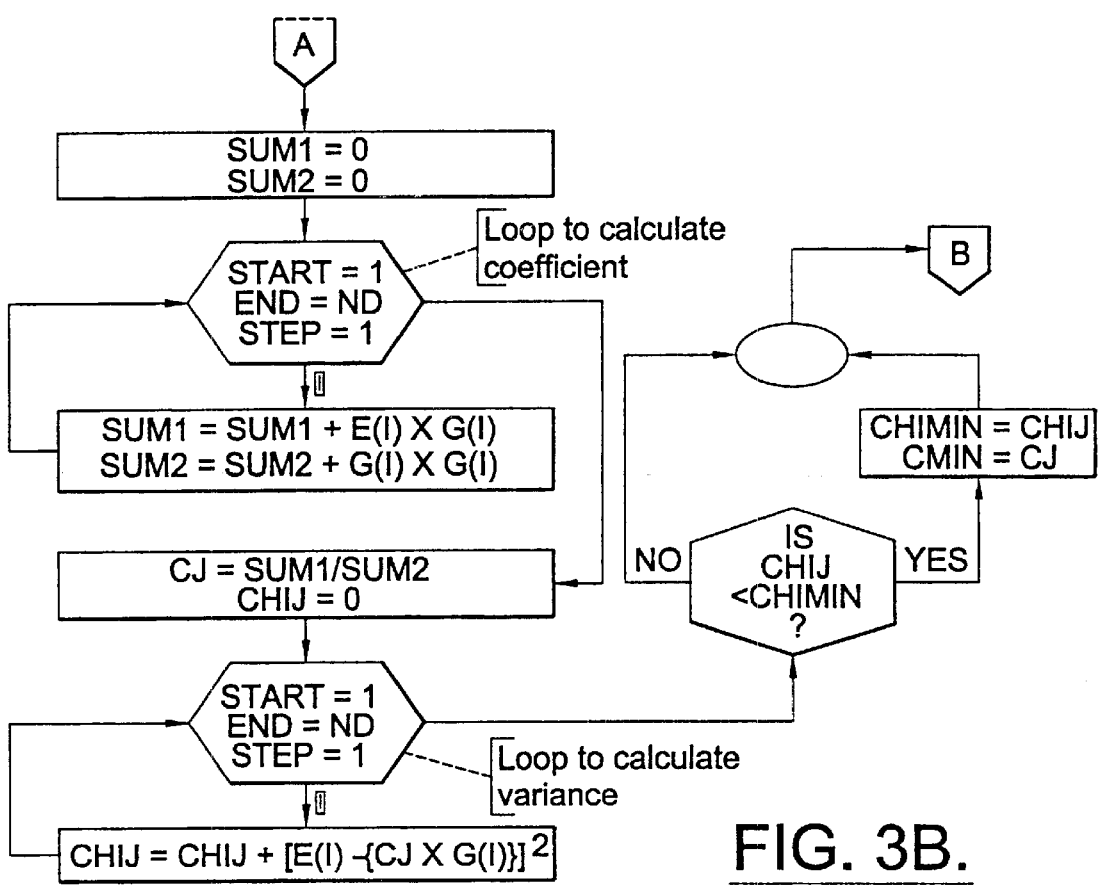

As seen in the flow charts of FIGS. 3A and 3B, the first step is to set up a counter from 1 to NDS (the number of data points to traverse to find the best least squares fit). The variable ICNT holds the loop counter. The variable J is the actual data point to start fitting. J increments with ICNT.

The counter is compared to NDS to see if the routine should continue. If it should continue, the glucose region of the analyte spectrum is read in to the array variable E.

The scaling constant CJ is calculated for this alignment according to the equations set forth below. CHIJ is calculated for these scaling constant. CHIJ is compared to CHIMIN, the minimum $\chi$ calculated so far. If CHIJ is lower than CHIMIN, then CHIMIN is set to CHIJ and the scaling constant for the lowest chi is retained in CMIN.

The starting data point J and the counter ICNT are increased by one and the loop is repeated. When the test ICNT>NDS is true, the concentration of glucose in the anlayte, Cglu, is calculated by multiplying the scaling factor CMIN from the best alignment by the known concentration of glucose in the standard spectrum, Sglu.

In calculating glucose concentration, the variables are provided as follows. $E_i$ is the intensity of the experimental spectrum at the ith data point. $G_i$ is the intensity of the standard glucose spectrum at the ith data point. The term "c" is the factor that relates the intensity of the standard spectrum to the intensity of the experimental spectrum.

Define $\chi$ as following:

$$\chi = \sum_i (E_i - cG_i)^2$$

and expand the polynomial to:

$$\chi = \sum_i (E_i^2 - 2cE_iG_i + c^2G_i^2)$$

$$\chi = \sum_i E_i^2 - 2c\sum_i E_iG_i + c^2\sum_i G_i^2$$

Perform a least squares fit:

$$\frac{\partial \chi}{\partial c} = 0$$

$$\frac{\sum_i E_i^2}{\partial c} - \left(2\sum_i E_iG_i\right)\frac{\partial c}{\partial c} + \left(\sum G_i^2\right)\frac{\partial c^2}{\partial c} = 0$$

$$\downarrow \qquad \qquad \downarrow$$

$$\frac{\sum_i E_i^2}{\partial c} = 0 \qquad \frac{\partial c}{\partial c} = 1$$

$$-2\sum_i E_iG_i + \left(\sum_i G_i^2\right)2c = 0$$

$$\sum_i E_iG_i = c\sum_i G_i^2$$

$$c = \frac{\sum_i E_iG_i}{\sum_i G_i^2}$$

The program moves one data point at a time to get the minimum chi→best alignment $$\sigma = \frac{1}{n}\chi^{1/2}$$

n=number of data points.

In any event, after the desired lipoprotein constituent parameters (such as the concentration of one or more lipoprotein subclass) and the glucose concentration in the blood are measured, at least one NMR-measured value, and preferably more than one NMR-measured value, is compared to one or more predetermined test criteria. From this comparison, the risk of the patient for developing Type 2 diabetes may be assessed.

Predetermined test criteria may be based on suitable values or definitions of normal or standard values of lipoprotein constituents, such as population-based norms or other targeted based norms. In a preferred embodiment, the population values are based on scientific results obtained from subjects in the Framingham Offspring Study. See Wilson et al., Impact of National Guidelines for Cholesterol Risk Factor Screening. The Framingham Offspring Study, JAMA, 1989; 262: 41–44. Of course the NMR-based lipoprotein constituent or subclass values presently defined for the assessment of risk may change over time and more or alternate risk categories may be added. Further, the actual ranges or definitions associated with the risk category values of one or more of the lipid panels or subclass categories may change over time and the present invention is not intended to be limited thereto.

In any event, preferred predetermined test criteria include small LDL size (Pattern B), which is a hallmark of the "diabetic lipoprotein phenotype" and confers approximately a two-fold higher risk compared to the large LDL trait (Pattern A). There is evidence that suggests that small LDL particles may be inherently more diabetogenic than large LDL. Low levels of large HDL (e.g., <29 mg/dL, a value corresponding to the 50$^{th}$ percentile of the population) may be a positive risk factor, as only larger HDL subclass particles appear to protect against diabetes—whereas small HDL may even be diabetogenic. Therefore, large HDL, rather than total HDL cholesterol, may be a more sensitive risk factor. See Freedman et al., *Arterioscler. Thromb. Vasc.*

*Biol.* 1998; 18:1046–53. Similarly, elevated levels of large triglyceride rich VLDL particles (e.g., >26 mg/dL, a value corresponding to the 75$^{th}$ percentile of the population) appear to be associated with increased risk for diabetes substantially independent of plasma triglycerides. High concentrations of large VLDL in fasting plasma may be a marker for delayed chylomicron clearance (postprandial lipemia).

If two out of the three risk factors presented above (i.e., pattern of small LDL, low level of large HDL and elevated level of large VLDL) are present in a patient's analysis, the patient may be considered to have diabetic dyslipidemia, a metabolic predisposition defined as a clustering of the lipoprotein subclass abnormalities set forth above. Such patients are considered to be at increased risk of developing Type 2 diabetes.

With regard to NMR-measured glucose levels, the glucose level measured is preferably a fasting blood glucose level, and is generally expressed in units of mg/dL. A desirable fasting glucose level is a value of less than about 90 mg/dL; a moderately elevated level of blood glucose is in the range of about 90–125 mg/dL; an elevated (i.e., diabetic or hyperglycemic) level is a glucose level over about 125 mg/dL. Patients with even moderately elevated fasting glucose levels are at an increased risk for developing Type 2 diabetes, particularly when they also have diabetic dyslipidemia as defined above.

As provided above, in one embodiment of the invention, at least one value of at least one lipoprotein constituent and preferably a value for plurality of lipoprotein constituents, is determined for a blood sample in order to assess the subjects risk of developing diabetes. The measured values of each lipoprotein constituent may be compiled into a profile of lipoprotein constituent values for that sample. Thus, the profile may, for example, illustrate a distribution of concentrations of lipoprotein subclasses for that sample. Additionally, the fasting glucose concentration present in the blood sample, as determined by the methods herein described, may also be included in the profile. The profile of NMR-measured values may be expressed graphically in a report in order to facilitate the visual comparison of a distribution of measured values with a distribution of standard test criteria. An example of such a report is shown in FIG. 4. The report is generated and presented essentially according to the method of generating reports set forth in co-assigned and co-pending U.S. application Ser. No. 09/258,740, the disclosure of which is incorporated herein in its entirety. FIG. 5 illustrates an additional report that may be generated during the performance of the NMR-based lipoprotein analysis; the generation of this report is also described in U.S. application Ser. No. 09/258,740. The report set forth in FIG. 5 may optionally be generated or prepared during the preparation of a report as shown in FIG. 4.

Other lifestyle and genetic information can also be acquired and factored into the risk assessment analysis. For example, weight, age, and family history of diabetes can all be assigned risk values which can be factored (separately or with) into the blood lipoprotein based analysis. A subject may have a borderline blood test risk assessment, but may be identified as being "at-risk" (i.e., for developing Type 2 diabetes) by the increased risk values attributed to one or more of familial, genetic, or lifestyle information. This information may then identify the subject for corrective action (drug therapy, exercise, weight loss or diet changes) and/or place the subject on a timed monitoring schedule. Alternatively, a subject with a borderline blood test risk assessment may be identified as being not at risk for developing Type 2 diabetes (or other insulin resistance disorder) if increased risk values attributed to genetic or lifestyle information are not present.

It will be understood by those skilled in the art that the methods described herein are useful for evaluating the efficacy of a treatment program for Type 2 diabetes or another disorder of insulin resistance. In such a method a blood sample is collected from a subject who is undergoing treatment for Type 2 diabetes or another disorder of insulin resistance. Alternatively, the subject may be an individual who has not yet begun such treatment, but will be undergoing the treatment in the future. A baseline profile of at least one parameter of at least one lipoprotein subclass is then obtained, by analyzing the blood sample by NMR spectral analysis as described herein. After the treatment has progressed, blood is again collected from the subject, and a second profile of the lipoprotein subclass parameters that were measured in the baseline profile is then obtained by NMR spectral analysis, as described herein. The second profile is compared to the baseline profile. A significant difference between the second profile and the baseline profile (as indicated by a significant difference between one or more measured parameters) provides an indication of the efficacy of treatment.

Figure 6:
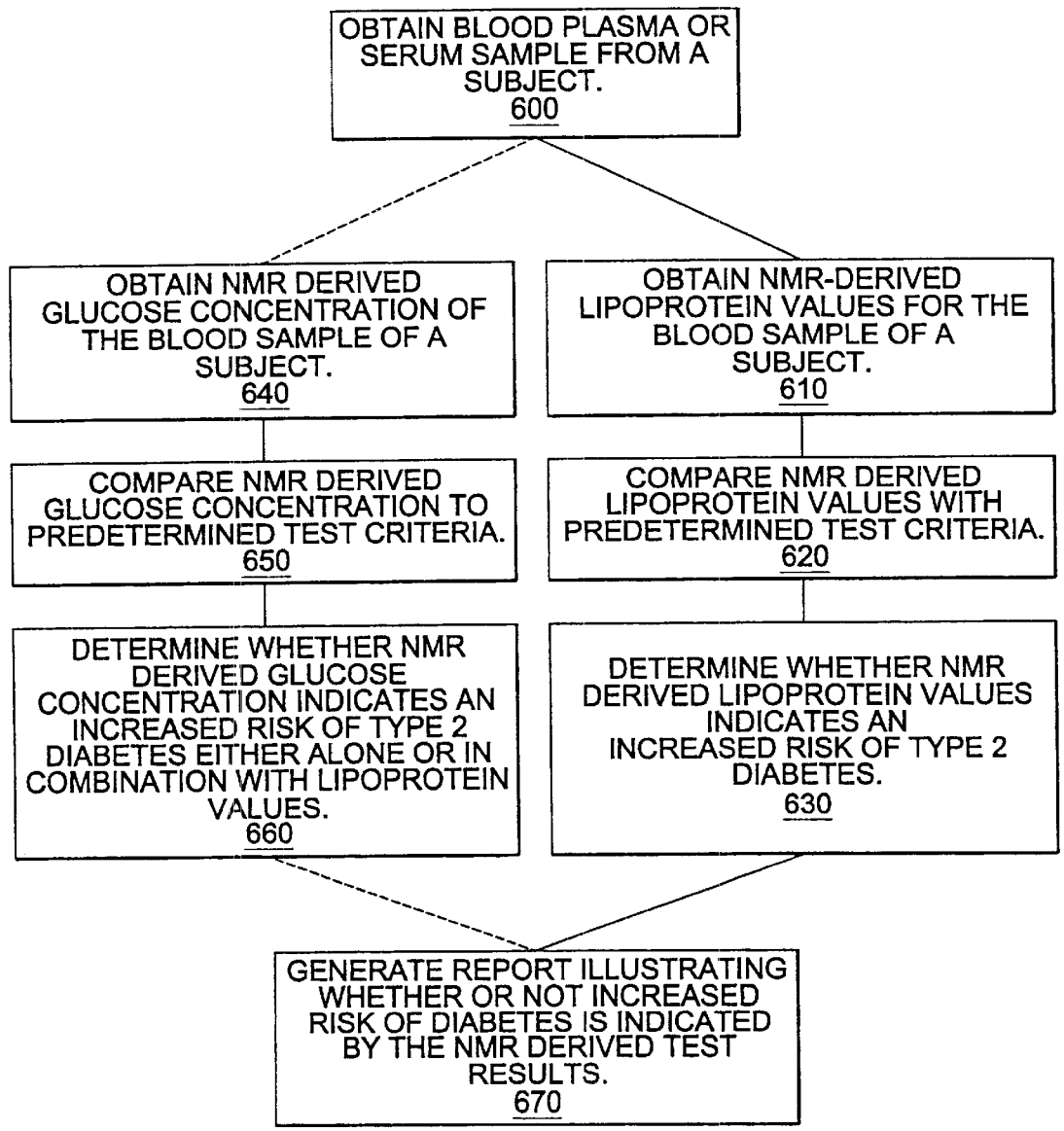
FIG. 6 is a flowchart of a method for performing the method of the present invention.

FIG. 6 illustrates a flow chart of methods, apparatus (systems) and computer program products according to the invention. It will be understood that each block of the flowchart illustration, and combinations of blocks in the flowchart illustrations, can be implemented by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce computer implemented process such that the instructions which execute on the computer or other programmable apparatus provide steps for implementing the functions specified in the flowchart block or blocks.

Accordingly, blocks of the flowchart illustrations support combinations of means for performing the specified functions and program instruction means for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer instructions.

As shown in FIG. 6, a blood plasma or blood serum sample (Block 600) is analyzed using NMR spectral analysis. NMR-derived lipoprotein values are obtained (Block 610) using the NMR techniques described herein. Preferably, an NMR spectral analysis is performed on a blood plasma sample and the lipoprotein values measured include selected subclass values. The NMR-derived lipoprotein value is compared to predetermined test criteria (Block 620) to determine whether the value is associated with an increased risk of developing Type 2 diabetes (Block 630). Preferably, the test criteria employed for the lipoprotein results (including the lipoprotein subclass values) correspond to a defined level of risk (low to high) of developing Type 2 diabetes. Preferably, the predetermined test criteria are based on scientific target "norms" or population based norms associated with higher or lower risks of Type 2 diabetes. These values may change over time or can be alternately identified for patients with increased secondary risk factors.

The blood plasma or blood serum sample of Block 600 may also and optionally and preferably can be used to obtain a NMR-derived glucose value (i.e., concentration of glucose in the sample) (Block 640). Once obtained, the NMR-derived glucose value is compared to predetermined test criteria (Block 650) to determine whether the value is associated with an increased risk of developing Type 2 diabetes (Block 660). The NMR-derived glucose value may be obtained concurrently with the NMR-derived lipoprotein value (i.e., the NMR spectral analysis for determining both the glucose value and the lipoprotein values may be performed on the same blood serum or blood plasma sample at the same time or within a short time period of the other).

After determining whether the NMR-derived glucose and NMR-derived lipoprotein constituent values are indicative of an increased risk of Type 2 diabetes, a report presenting the results of the analysis of the NMR-derived glucose and NMR-derived lipoprotein constituent values may be generated (Block 670). This report may contain, e.g., the NMR-measured values themselves, the risk assessment itself, or any other presentation of information determined or obtained during the Type 2 diabetes risk assessment.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A method for assessing a patient's risk of having or developing Type 2 diabetes and/or insulin resistance disorders based on NMR-derived lipoprotein-based information, comprising the steps of:

obtaining at least one proton NMR spectroscopic signal of a patient's blood plasma or serum sample to perform a NMR spectral analysis thereof;

deriving a NMR-based lipoprotein measurement value for a plurality of selected lipoprotein subclass constituents of interest based on said obtaining step;

comparing the NMR-based measured lipoprotein subclass constituent values to predetermined test criteria, wherein the predetermined test criteria define at least one lipoprotein constituent value or range of values having an unfavorable or positive risk factor associated therewith, for each of the plurality of selected lipoprotein subclass constituents of interest; and assessing a patient's risk of having or developing at least one of Type 2 diabetes and/or insulin resistance disorders based on the number of and/or degree of risk associated with individual lipoprotein subclass constituent values having an unfavorable or positive risk factor identified in said comparing step.

2. A method according to claim 1, further comprising:

concurrently generating a NMR-based glucose measurement value for the patient's blood plasma or serum sample by considering NMR data from a plurality of peaks in the 3.1–3.9 region of the proton-NMR spectrum;

comparing the NMR-based glucose measurement value to predetermined test criteria; and determining the patient's risk of developing or having insulin resistance or Type 2 diabetes based, at least in part, on the detection of an elevated glucose level.

3. A method according to claim 2, wherein said step of comparing comprises comparing the NMR-based measured values associated with the selected lipoprotein subclass constituents of at least a plurality of the subclass constituents of the group consisting of: LDL particle size, large HDL concentration, LDL particle concentration, and large VLDL concentration to respective predetermined test criteria and wherein said assessing step is based on the presence of both the determination of the presence of an unfavorable or positive risk factor for a plurality of the selected lipoprotein subclass constituents and the detection of an elevated glucose level.

4. A method according to claim 3, wherein the unfavorable or positive risk factor for LDL particle size in the predetermined test criteria identifies the LDL size as Pattern B.

5. A method according to claim 3, wherein the large HDL concentration predetermined test criteria that defines an unfavorable or positive risk factor identifies a low level of large HDL concentration.

6. A method according to claim 3, wherein the large VLDL concentration predetermined test criteria identifies an elevated level of large VLDL concentration.

7. A method according to claim 3, wherein said comparing step used to identify the patient as having or being at risk for having Type-2 diabetes and/or insulin resistance disorders is based on a positive risk test match for at least three of the selected NMR based lipoprotein subclass constituent measured values.

8. A method according to claim 2, further comprising the step of determining whether the sample indicates the presence of diabetic dyslipidemia in the patient based on said comparing and assessing steps, and wherein the presence of diabetic dyslipidemia is determined based on an unfavorable value for at least two of the measured lipoprotein constituent subclass values as defined by the predetermined test criteria and when the NMR-based glucose measurement value indicates an elevated level of blood glucose.

9. A method according to claim 1, further comprising the step of determining whether the sample indicates the presence of Type 2 diabetes, insulin related disorders, and/or diabetic dyslipidemia in the patient based on said comparing and assessing steps, and wherein the NMR-based lipoprotein constituent values used includes values associated with positive risk factors for at least a plurality of the lipoprotein subclass constituents comprising LDL particle size, LDL particle concentration, large HDL concentration, and large VLDL concentration.

10. A method according to claim 1, wherein the selected lipoprotein subclass constituents of the deriving step comprise at least two of LDL particle size, LDL particle concentration, large HDL concentration, and large VLDL concentration, and wherein the positive or unfavorable predetermined test criteria of the comparing step identifies the LDL particle size test criteria as Pattern B, the large HDL concentration as a low level of large HDL concentration, and the large VLDL concentration as an elevated level of large VLDL concentration, and wherein the presence of an at-risk condition for Type 2 diabetes and/or insulin related disorders is determined in the assessing step based on the positive identification of at least two of the NMR lipoprotein based constituent values to the predetermined test criteria.

11. A method according to claim 1, wherein the assessing step is carried out so that an at-risk condition is identified when a plurality of lipoprotein subclass constituents have unfavorable or positive risk values.

12. A method according to claim 11, wherein the lipoprotein subclass constituents and associated risk values denoted with unfavorable or positive risk includes at least two of: a low large HDL concentration, an elevated LDL particle concentration, a small LDL particle size, and an elevated large VLDL concentration.

13. A method for assessing a patient's risk of developing or having insulin resistance syndrome, insulin resistance disorders, and/or Type-2 diabetes, based on NMR measured lipoprotein-based information, comprising the steps of:

obtaining at least one proton NMR spectroscopic signal of a patient's blood plasma or serum sample to perform a NMR spectral analysis thereof;

deriving a NMR-based lipoprotein measurement value for a plurality of lipoprotein subclass constituents based on said obtaining step;

comparing the NMR-based measured lipoprotein subclass constituent values to predetermined test criteria, wherein the predetermined test criteria define unfavorable or positive risk factors for each of the lipoprotein subclass constituents of interest which are associated with insulin resistance syndrome, insulin resistance disorders and/or Type 2 diabetes; and assessing a patient's risk of developing or having insulin resistance syndrome, insulin resistance disorders, and/or Type-2 diabetes based on the number of and/or degree of risk associated with the plurality of individual lipoprotein subclass constituents that are identified as having an unfavorable or positive risk factor in said comparing step.

14. A method according to claim 13, further comprising:

concurrently generating at least one NMR-based glucose measurement value for the patient's blood plasma or serum sample based on the NMR spectral analysis of said obtaining step, the glucose measurement comprises evaluating the amplitudes of a plurality of peaks in the portion of the NMR spectrum between about 3.1–3.9 ppm;

comparing the NMR-based glucose measurement value to predetermined test criteria that defines elevated levels of glucose; and wherein said assessing step further considers the detection of elevated glucose from said comparing step.

15. A method according to claim 14, wherein the patient is identified as being at risk for having or developing insulin resistance disorders, insulin resistance syndrome and/or diabetes when both (a) the NMR-based glucose measurement value is an elevated level of blood glucose; and (b) the concurrent positive identification that at least two of the lipoprotein based constituent subclass values are unfavorable according to the predetermined test criteria.

16. A method according to claim 13, wherein the NMR-based lipoprotein subclass constituent values of said deriving and comparing steps comprise the values associated with LDL particle size, LDL particle concentration, large HDL concentration, and large VLDL concentration.

17. A method according to claim 13, wherein said step of comparing a plurality of NMR-based lipoprotein subclass constituent values comprises comparing at least a plurality of the NMR measured values associated with LDL particle size, LDL particle concentration, large HDL concentration, and large VLDL concentration to respective predetermined test criteria.

18. A method according to claim 17, wherein the LDL particle size predetermined test criteria identifies the LDL particle size as Pattern B.

19. A method according to claim 17, wherein the large HDL concentration-predetermined test, criteria identifies a low level of large HDL concentration.

20. A method according to claim 17, wherein the large VLDL concentration predetermined test criteria identifies an elevated level of large VLDL concentration.

21. A method according to claim 17, wherein said comparing step is carried out to determine if there is a positive test match representative of an unfavorable risk factor for at least two of the identified NMR based lipoprotein subclass constituent values.

22. A method according to claim 17, wherein the step of comparing compares the measured values of LDL particle size, LDL particle concentration, large HDL concentration, and large VLDL concentration, and wherein the LDL particle size predetermined test criteria identifies the LDL particle size as pattern B, the large HDL concentration predetermined test criteria identifies a low level of the large HDL concentration, the LDL particle concentration predetermined test criteria identifies the LDL particle concentration as elevated, and the large VLDL concentration test criteria identifies an elevated level of large VLDL concentration, and wherein the assessing step is determined based on the identification that at least two of these measured lipoprotein subclass constituent values are unfavorable risk factors as defined by the predetermined test criteria.

23. A method of evaluating the efficacy of treatment of a subject undergoing treatment for insulin resistance disorders, insulin resistance syndrome, and/or Type 2 diabetes based on personalized NMR measured lipoprotein information, comprising:

obtaining a baseline profile including measured values for a plurality of lipoprotein subclass constituents in a patient's blood plasma or serum sample, wherein the baseline profile is derived from a proton NMR spectral analysis of a NMR spectroscopic signal of the patient's blood plasma or serum sample which measures lipoprotein constituent values of concentration or size, wherein the baseline profile includes a risk assessment analysis that considers the number of lipoprotein subclass constituent values that have an unfavorable risk factor associated therewith according to predetermined risk criteria to identify whether the patient is at risk for having or developing insulin resistance related disorders, insulin resistance syndrome, and/or Type-2 diabetes;

obtaining a second profile of proton NMR measured lipoprotein subclass constituent values for a patient's blood plasma or serum sample after the subject has undergone treatment for insulin resistance related disorders, insulin resistance syndrome and/or Type 2 diabetes; and automatically comparing the second profile with the baseline profile to identify differences in the lipoprotein subclass constituent measurements and/or risk analysis therebetween, wherein a difference between the second profile and the baseline profile of the subject provides an indication of the efficacy of treatment for insulin resistance related disorders, insulin resistance syndrome, and/or Type 2 diabetes of the subject.

24. The method according to claim 23, wherein the proton NMR spectral analysis of the baseline profile and the second profile are carried out to provide a glucose measurement value for the patient's blood plasma or serum sample, wherein the glucose measurement is obtained concurrently with the proton NMR measured lipoprotein constituent values of the subject by evaluating the amplitudes of a plurality of peaks in the portion of the NMR spectrum between about 3.1–3.9 ppm.

25. An NMR-based method for measuring the concentration of glucose concentration of blood plasma or serum specimen, comprising the steps of:
 acquiring a reference data spectrum in a region of interest corresponding to glucose in a reference blood plasma or serum specimen;
 determining a reference glucose lineshape in the reference spectrum based on at least one signal in the reference spectrum, wherein the reference glucose lineshape spectrum in blood plasma comprises a plurality of peaks within a region extending between about 3.1–3.9 ppm of a proton NMR spectrum of the blood plasma or serum specimen;
 assigning a reference coefficient to the reference glucose lineshape in the reference spectrum;
 acquiring an NMR spectrum of a patient's blood plasma or serum specimen corresponding to the region of interest in the reference specimen, the patient spectrum comprising a plurality of peaks within a region extending between about 3.1–3.9 ppm;
 identifying a patient glucose lineshape with the plurality of peaks in about the 3.1–3.9 ppm region of the spectrum for the patient specimen in the patient NMR spectrum based on the same at least one signal used to determine the reference glucose lineshape in the reference spectrum;
 comparing the reference glucose lineshape with the patient glucose lineshape;
 fitting the amplitudes of the plurality of peaks in the reference glucose lineshape to the plurality of peaks in the patient glucose lineshape in the region extending between about 3.1–3.9 ppm;
 calculating a scaling factor based on said fitting step; and
 determining the concentration of glucose in the patient blood plasma or serum specimen as a function of the value of the scaling factor and reference coefficient.

26. A method according to claim 25, wherein the value of the reference coefficient is based on an independent chemical measurement of glucose concentration of the reference specimen.

27. A method according to claim 25, wherein the NMR reference and patient spectrums are obtained at substantially the same magnetic field strength and same specimen temperature.

28. A method according to claim 25, wherein the glucose reference spectrum is within a region extending between about 3.64–3.90 ppm of the proton NMR spectrum of blood plasma.

29. A method according to claim 25, wherein the glucose reference spectrum is within a region extending between about 3.29–3.54 ppm of the proton NMR spectrum of blood plasma.

30. A method according to claim 25, wherein the glucose reference spectrum is within at least one of two regions of interest of the proton NMR spectrum of blood plasma or serum, a first region extending between about 3.64–3.90 ppm and a second region extending between about 3.29–3.54 ppm.

31. A computer program product for determining whether a subject is at risk for having or developing insulin resistance disorders and/or Type 2 diabetes, comprising a computer-readable storage medium having computer-readable program code means embodied in the medium, the computer-readable program code means comprising:
 computer code means for generating a proton NMR spectrum and measuring the values associated with concentration or size of a plurality of lipoprotein subclass constituents for a patient's blood plasma or serum sample;
 computer code means for comparing a plurality of NMR-measured lipoprotein subclass constituent values to predetermined test criteria defined as an unfavorable value or range of values for selected lipoprotein subclass constituents; and
 computer code means for assessing a patient's risk of developing or having Type 2 diabetes and/or insulin resistance disorders based on the number of individual lipoprotein subclass constituents identified as having an unfavorable or positive risk factor associated with the measured values.

32. The computer program product of claim 31, further comprising:
 computer code means for concurrently generating a proton NMR spectral analysis of a proton NMR spectrum to define the glucose level for the patient's blood plasma or serum sample, wherein the computer code means comprises generating a patient glucose lineshape having a plurality of peaks that rise and fall in relation to the concentration of glucose, the peaks residing in a portion of the spectrum between about 3.1 to 3.9 ppm, comparing the glucose spectrum to a glucose reference lineshape having an associated amplitude, fitting the amplitude of the reference glucose lineshape to the patient glucose lineshape and determining the concentration of glucose in the patient blood plasma or serum specimen;
 computer code means for comparing the measured glucose concentration to predetermined test criteria to assess whether the glucose measurement is elevated; and
 computer code means for assessing the patient's risk of having or developing insulin resistance disorders and/or Type 2 diabetes which considers the presence of an elevated glucose level.

33. A screening test method for concurrently screening a patient for the risk of coronary heart disease and insulin resistance or Type-2 diabetes, comprising the steps of:
 performing a proton NMR spectral analysis of a patient's blood plasma or serum sample, the spectral analysis producing a spectrum having a plurality of peaks in the region between about 3.1–3.9 ppm;
 measuring a plurality of lipoprotein subclass constituent values based on said performing step;
 assessing the patient's risk of coronary heart disease based on said measuring step;
 concurrently measuring a glucose level in the sample based on said performing step by evaluating a plurality of the peaks in the 3.1–3.9 ppm region of the spectrum;
 determining the patient's risk of developing or having Type 2 diabetes or insulin resistance disorders based on said measuring steps; and
 generating an individualized patient report presenting the risk of having or developing coronary heart disease and insulin resistance and/or Type-2 diabetes.

34. A screening test method of claim 33, further comprising assessing the risk of developing gestational diabetes.

35. A screening test method of claim 33, further comprising assessing the risk of developing juvenile diabetes.

36. A method for concurrently obtaining measurement data to assess both the risk of CHD and insulin resistance or related disorders and/or Type-2 diabetes for a patient, comprising:

obtaining data associated with at least one NMR spectroscopic signal of an in vitro sample of a patient's blood or serum to perform a NMR spectral analysis thereof;

deriving a plurality of NMR-based measurements for a plurality of different lipoprotein subclass constituents comprising at least two of LDL particle size, LDL particle concentration, large HDL concentration, and large VLDL concentration;

evaluating the patient's risk of having or developing coronary heart disease (CHD) based on selected measurements obtained from said obtaining and deriving steps based on predetermined CHD test criteria; and concurrently determining the patient's risk of having or developing insulin resistance related disorders and/or Type-2 diabetes based on selected measurements obtained from said deriving step and based on predetermined test criteria for insulin resistance related disorders and/or Type-2 diabetes, wherein the test criteria defines values and their associated degree of risk, including increased and decreased values, for the selected lipoprotein subclass constituent measurements and the risk is determined to be present when a plurality of the selected lipoprotein subclass constituents present with increased risk values.

37. A method according to claim 36, wherein the evaluating and determining steps consider at least one common lipoprotein particle subclass constituent value.

38. A method according to claim 36, further comprising concurrently generating a NMR-based glucose measurement value for the patient's blood plasma or serum sample by evaluating NMR data from a plurality of peaks in the 3.1–3.9 region of the proton NMR spectrum; and comparing the NMR-based glucose measurement value to predetermined test criteria;

wherein said determining step considers the glucose value in establishing the patient's risk of having or developing insulin resistance related disorders and/or Type-2 diabetes.

39. A method according to claim 36, wherein said evaluating and determining steps are performed based on NMR data gathered simultaneously on the same patient sample.

40. A screening method for concurrently assessing a patient's risk of having or developing coronary heart disease and/or insulin resistance related disorders and/or Type-2 diabetes, comprising:

measuring a plurality of lipoprotein subclass constituents in a patient's blood or plasma sample using NMR spectroscopy-derived data, the lipoprotein subclass constituent measurements being carried out to measure at least two of: LDL particle size, LDL particle concentration, large HDL concentration, and/or large VLDL concentration;

evaluating the patient's risk of having or developing coronary heart disease (CHD) based on predetermined CHD test criteria using selected measurements obtained from said measuring step;

determining the patient's risk of having or developing insulin resistance related disorders and/or Type-2 diabetes based on predetermined insulin resistance related disorders and/or Type-2 diabetes test criteria using selected measurements obtained from said measuring step; and repeating said measuring, evaluating, and determining steps for a plurality of different patients to provide a mass screening test that is able to identify at-risk patients.

41. A method according to claim 40, further comprising measuring glucose in the patient's blood or plasma sample using NMR spectroscopy derived data that includes data that corresponds to a plurality of peaks in about the 3.1–3.9 portion of a NMR proton spectrum.

42. A method according to claim 40, wherein the lipoprotein subclass constituents and associated risk values denoted with unfavorable or positive risk includes at least two of: a low large HDL concentration, an elevated LDL particle concentration, a small LDL particle size, and an elevated large VLDL concentration.

43. A mass screening method for assessing a patient's risk of having or developing Type 2 diabetes and/or insulin resistance disorders, comprising:

deriving a respective No spectroscopy based lipoprotein measurement value for each of a plurality of selected lipoprotein subclass constituents of interest in a blood plasma or serum sample of a patient;

comparing the measured lipoprotein subclass constituent values to predetermined test criteria, wherein the predetermined test criteria define a respective lipoprotein subclass constituent value or range of values having an unfavorable or positive risk factor associated therewith for each of the plurality of selected lipoprotein subclass constituents of interest;

assessing the patient's risk of having or developing at least one of Type 2 diabetes and/or insulin resistance disorders based on the number of individual lipoprotein subclass constituents having an unfavorable or positive risk factor identified in said comparing step; and automatically repeating the deriving, comparing, and assessing steps for a plurality of different patient samples to thereby perform a mass screening test that is able to identify at-risk patients.

44. A method according to claim 43, further comprising measuring glucose in the patient's blood or plasma sample using NMR spectroscopy derived data that includes data that corresponds to a plurality of peaks in about the 3.1–3.9 portion of a NMR proton spectrum.

45. A method according to claim 43, wherein the lipoprotein subclass constituents and associated risk values denoted with unfavorable or positive risk includes at least two of: a low large HDL concentration, an elevated LDL particle concentration, a small LDL particle size, and an elevated large VLDL concentration.

* * * * *

UNITED STATES PATENT AND TRADEMARK OFFICE
CERTIFICATE OF CORRECTION

PATENT NO. : 6,518,069 B1
DATED : February 11, 2003
INVENTOR(S) : Otvos et al.

It is certified that error appears in the above-identified patent and that said Letters Patent is hereby corrected as shown below:

<u>Column 22,</u>
Line 29, should read as follows -- deriving a respective NMR spectroscopy based lipoprotein --

Signed and Sealed this

Twenty-second Day of June, 2004

JON W. DUDAS
*Acting Director of the United States Patent and Trademark Office*